(12) United States Patent
Chung et al.

(10) Patent No.: US 10,241,089 B2
(45) Date of Patent: Mar. 26, 2019

(54) ULTRASONIC PROBE, METHOD OF WORKING THE SAME, AND MOUNTING DEVICE

(71) Applicant: SAMSUNG ELECTRONICS CO., LTD., Suwon-si (KR)

(72) Inventors: Hae-in Chung, Anyang-si (KR); Tae-kyung Kim, Seongnam-si (KR); Su-kwang Lim, Gwangmyeong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 465 days.

(21) Appl. No.: 14/851,040

(22) Filed: Sep. 11, 2015

(65) Prior Publication Data

US 2016/0077059 A1    Mar. 17, 2016

(30) Foreign Application Priority Data

Sep. 15, 2014   (KR) .................. 10-2014-0122032

(51) Int. Cl.
*G01N 29/32*   (2006.01)
*G01N 29/24*   (2006.01)
*A61B 8/00*   (2006.01)

(52) U.S. Cl.
CPC ......... *G01N 29/326* (2013.01); *A61B 8/4444* (2013.01); *A61B 8/546* (2013.01); *G01N 29/2406* (2013.01); *A61B 8/4411* (2013.01); *A61B 8/4483* (2013.01); *A61B 8/56* (2013.01)

(58) Field of Classification Search
CPC .. G01N 29/326; G01N 29/2406; A61B 8/546; A61B 8/4483; A61B 8/4411; A61B 8/4444; A61B 8/56
See application file for complete search history.

(56) References Cited

U.S. PATENT DOCUMENTS

| | | | |
|---|---|---|---|
| 6,876,550 B2 | 4/2005 | Sri-Jayantha et al. | |
| 7,188,484 B2 | 3/2007 | Kim | |
| 7,254,019 B2 | 8/2007 | Leu et al. | |
| 2006/0191344 A1* | 8/2006 | Hashimoto | A61B 8/00 73/632 |
| 2009/0112099 A1* | 4/2009 | Kurokawa | A61B 8/00 600/459 |
| 2012/0006994 A1* | 1/2012 | Niekawa | A61B 6/4233 250/370.08 |
| 2014/0102662 A1* | 4/2014 | Grama | F28D 20/00 165/10 |
| 2016/0029835 A1* | 2/2016 | Zwart | A47J 31/10 99/281 |
| 2017/0135674 A1* | 5/2017 | Wang | A61B 8/4472 |

FOREIGN PATENT DOCUMENTS

JP  2001236145 A  8/2001
JP   200692894 A  4/2006

* cited by examiner

*Primary Examiner* — Xin Y Zhong
(74) *Attorney, Agent, or Firm* — Sughrue Mion, PLLC

(57) ABSTRACT

An ultrasonic probe, a method of operating the same, and a mounting device are provided. The ultrasonic probe includes a main body configured to transmit and receive ultrasound, a heat storage including a phase-change material configured to store heat being generated by the main body, and a display configured to display an amount of the stored heat.

15 Claims, 13 Drawing Sheets

ULTRASONIC PROBE, METHOD OF WORKING THE SAME, AND MOUNTING DEVICE

CROSS-REFERENCE TO RELATED APPLICATION

This application claims priority from Korean Patent Application No. 10-2014-0122032, filed on Sep. 15, 2014, in the Korean Intellectual Property Office, the disclosure of which is incorporated herein in its entirety by reference.

BACKGROUND

1. Field

Apparatuses and methods consistent with exemplary embodiments relate to an ultrasonic probe, a method of operating the same, and a mounting device.

2. Description of the Related Art

An ultrasonic diagnostic imaging apparatus is an apparatus that emits ultrasound from a surface of an object into a target region inside the object, receives a reflected ultrasonic echo signal, and noninvasively obtains an image of blood flow or a tomogram of soft tissue.

When compared to other diagnostic imaging apparatuses such as a radiographic imaging apparatus using X-rays, a computerized tomography (CT) scanner, a magnetic resonance imaging (MRI) apparatus, and a nuclear medicine diagnostic imaging apparatus, an ultrasonic diagnostic imaging apparatus is small, inexpensive, and may display a diagnostic image in real time. Also, because an ultrasonic diagnostic imaging apparatus has no risk of radiation exposure, the ultrasonic diagnostic imaging apparatus has high stability. Accordingly, an ultrasonic diagnostic imaging apparatus is widely used to monitor the heart, an abdominal organ, and a urinary tract or urogenital system as well as a fetus in a pregnant woman.

An ultrasonic diagnostic imaging apparatus includes an ultrasonic probe that transmits ultrasound to an object and receives an ultrasonic echo signal reflected from the object to obtain an image of an internal body structure of the object.

In general, a piezoelectric material that generates ultrasound by converting electrical energy into mechanical vibration energy is widely used as a material for a transducer that generates ultrasound in an ultrasonic probe.

A capacitive micromachined ultrasonic transducer (cMUT) that is a concept in the field of transducers has been developed.

A cMUT that is an ultrasonic transducer for transmitting/receiving ultrasound by using vibration of hundreds or thousands of micromachined membranes is manufactured based on micro-electro-mechanical system (MEMS) technology. A capacitor is formed by forming a lower electrode and an insulating layer on a semiconductor substrate that is used during a general semiconductor process, forming an air-gap on the insulating layer including the lower electrode, forming a membrane having a thickness that is several to thousands of Å on the air-gap, and forming an upper electrode on the membrane.

When alternating current (AC) is applied to the capacitor, the membrane begins to vibrate and thus ultrasound is generated. In contrast, when the membrane is forced to vibrate due to external ultrasound, the capacitance of the capacitor changes. Ultrasound is received by detecting the change in capacitance.

Because one cMUT has a diameter that is just tens of μm, an array of tens of thousands of cMUTs has a size that is just several mm. Also, because tens of thousands of sensors may be simultaneously accurately arranged at desired positions by using one semiconductor manufacturing process and cMUT elements are connected to application specific integrated circuits (ASICs) by using chip bonding such as flip-chip bonding to apply an electrical signal to a cMUT, process complexity due to wiring may be overcome.

Due to such advantages, a cMUT is suitably used to manufacture a 2D array of transducers that is a trend, and helps to develop a multi-channel transducer.

The amount of heat that is generated by an electrical circuit for driving a probe including a relatively small number of channels of transducers is just about 1 W, which is small enough to be naturally released through a case of the probe. However, the amount of heat that is generated when multi-channel transducers are included is as much as about 7 W. Accordingly, there is a demand for a technology for dissipating heat from an ultrasonic probe and cooling the ultrasonic probe.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include an ultrasonic probe that displays on a display the amount of heat that is stored in a heat storage that is disposed to dissipate heat of the ultrasonic probe, and thus enables an operator to check a temperature of the ultrasonic probe and the amount of heat that remains in the heat storage and to determine an operation condition and an operation time based on the temperature and the amount of remaining heat, and a method of working the ultrasonic probe.

One or more exemplary embodiments include a mounting device including a heat dissipator and a charger.

According to an aspect of an exemplary embodiment, an ultrasonic probe includes a main body configured to transmit and receive ultrasound, a heat storage including a phase-change material configured to store heat being generated by the main body, and a display configured to display an amount of the stored heat.

The ultrasonic probe may further include a battery configured to supply power to the main body.

The battery may be configured to be attached to the heat storage, and the battery and the heat storage may be configured to be attached to and detached from the main body.

The heat storage may include a piston configured to move according to a change in a volume of the phase-change material, and the battery may include a switch configured to control an electrical connection with the main body, and turn on and turn off according to the movement of the piston.

The switch may include a first connection part, and a second connection part configured to contact the first connection part to turn on the switch, and separate from the first connection part to turn off the switch, according to the movement of the piston.

The heat storage may further include an elastic member configured to move and contact the second connection part, according to the movement of the piston, and the second connection part may be configured to separate from the first connection part to turn off the switch, according to the movement and the contact of the elastic member.

The switch may be configured to turn off to cut off the power to the main body in response to a phase change of the phage-change material being complete.

The ultrasonic probe may further include a sensor configured to detect the movement of the piston, and detect the change in the volume of the phase-change material.

The display may be configured to change in color, according to the detected change in the volume of the phase-change material.

The heat storage may further include a housing configured to change in color, according to the detected change in the volume of the phase-change material.

The display may be configured to display the movement of the piston.

A temperature of a phase-change may be greater than or equal to 25° C. and is less than or equal to 37° C.

A mounting device on which the ultrasonic probe is mounted, includes an insertion part into which the heat storage is inserted, and a heat dissipator configured to dissipate the stored heat.

The ultrasonic probe may further include a battery configured to supply power to the main body, and the mounting device may further include a charger configured to charge the battery.

The charger may be configured to charge the battery, using a wireless or wired method.

The dissipation of the stored heat by the heat dissipator and the charge of the battery by the charger may be simultaneously performed.

The display may be configured to display an amount of the dissipated heat.

According to an aspect of an exemplary embodiment, there is provided a method of using an ultrasonic probe including a main body, a phase-change material, and a display, the method including checking a state of the phase-change material storing heat being generated by the main body transmitting and receiving ultrasound, using the display, inputting an operation condition of the ultrasonic probe according to the state of the phase-change material, and determining a working time of the main body according to the state of the phase-change material and the operation condition.

The operation condition may be at least one among a number of objects to be operated, an operation type, a frame speed of the main body, and a number of channels.

According to an aspect of an exemplary embodiment, an ultrasonic probe includes a main body configured to transmit and receive ultrasound, a phase-change material configured to store heat being generated by the main body, and a display configured to display a state of the phase-change material.

BRIEF DESCRIPTION OF THE DRAWINGS

The above and/or other aspects will become more apparent by describing exemplary embodiments with reference to the accompanying drawings, in which.

DETAILED DESCRIPTION

Figure 1:
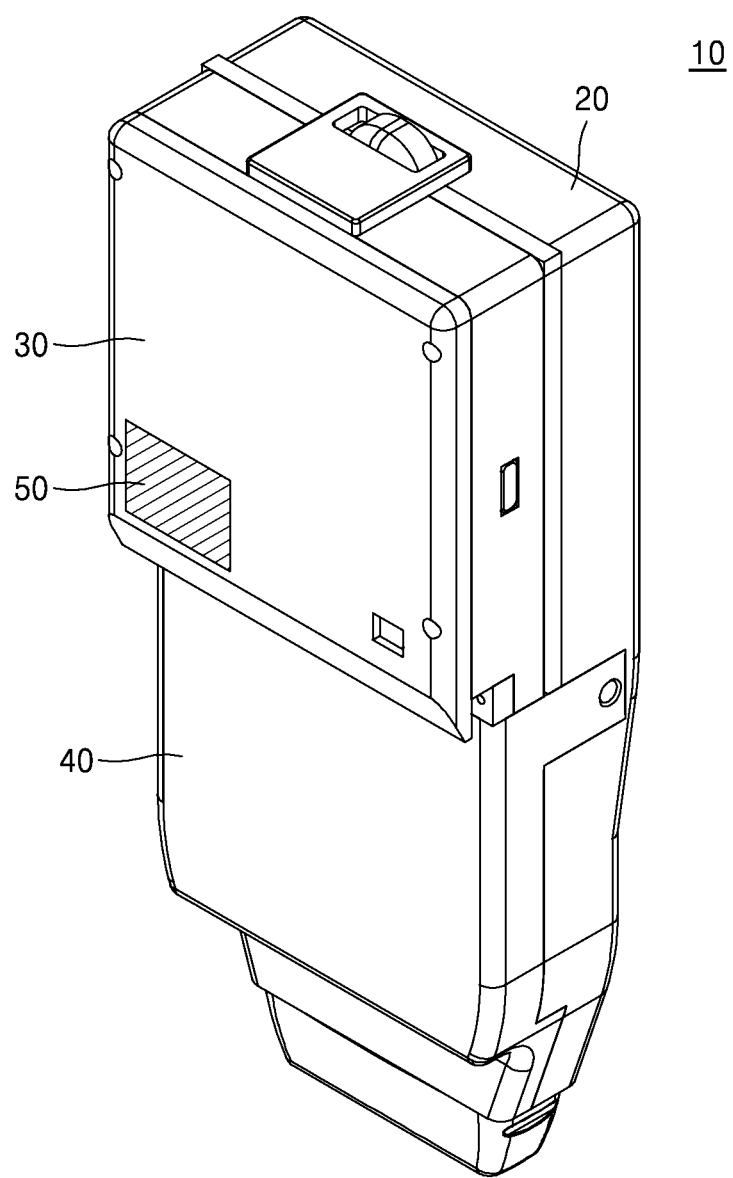
FIG. 1 is a perspective view illustrating an ultrasonic probe according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions may not be described in detail because they would obscure the description with unnecessary detail.

The term such as " . . . unit" used herein indicates a unit, which processes at least one function or motion, and the unit may be implemented by hardware or software, or by a combination of hardware and software.

The term "object to be operated" used herein may include a human, an animal, or a body part of a human or an animal. For example, the object to be operated may include an organ such as the liver, heart, womb, brain, breast, or stomach, or a blood vessel. Also, the term "operator" used herein may refer to, but is not limited to, a medical expert such as a doctor, a nurse, a clinical pathologist, a medical image expert, or an engineer who repairs a medical device.

As used herein, the term "and/or" includes any and all combinations of one or more of the associated listed items. Expressions such as "at least one of," when preceding a list of elements, modify the entire list of elements and do not modify the individual elements of the list.

Figure 2:
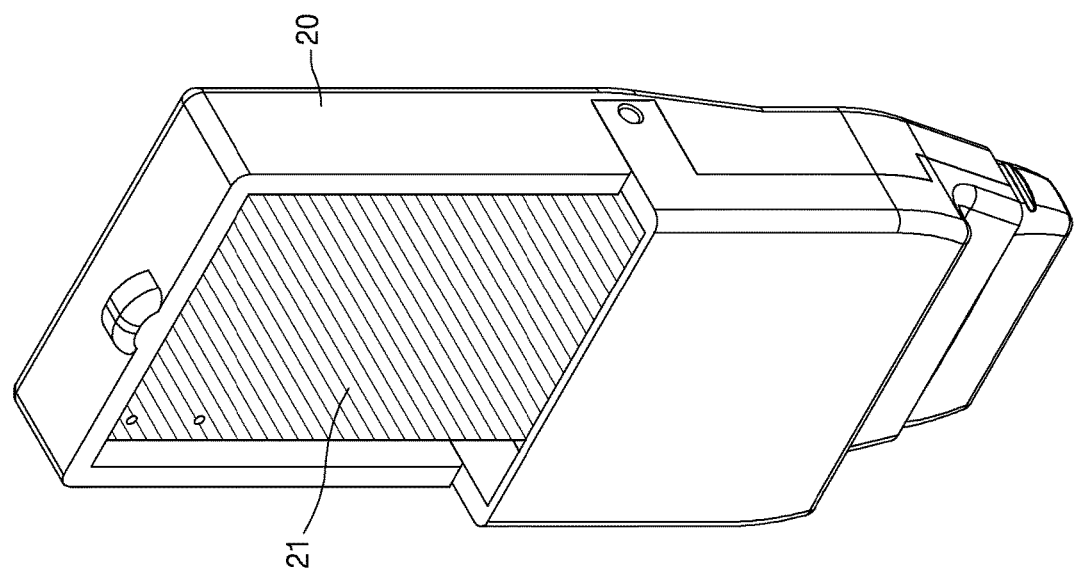
FIG. 2 is an exploded perspective view illustrating the ultrasonic probe of FIG. 1.
Figure 2:
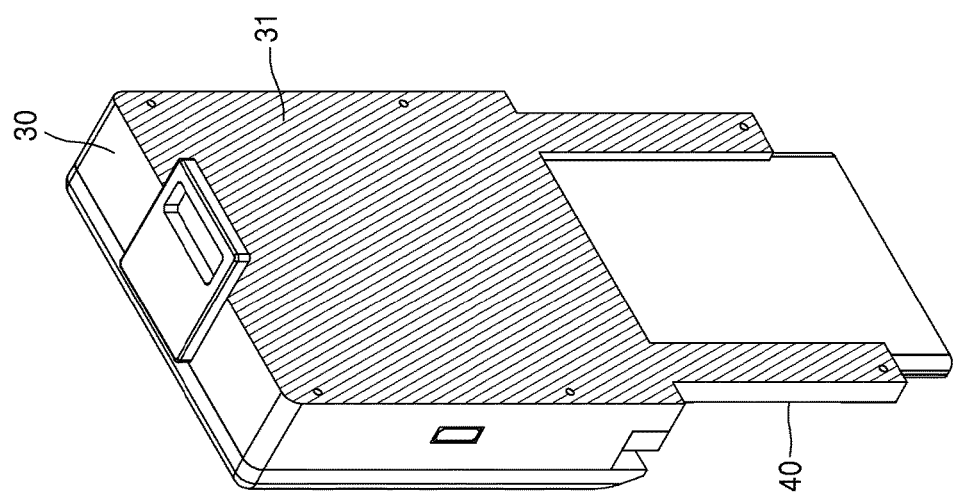

FIG. 1 is a perspective view illustrating a structure of an ultrasonic probe 10 according to an exemplary embodiment. FIG. 2 is an exploded perspective view illustrating the ultrasonic probe 10 of FIG. 1.

Referring to FIG. 1, the ultrasonic probe 10 includes a main body 20 that transmits an ultrasound signal to an object to be operated and receives an echo signal reflected from the object to be operated, and a heat storage 30 that stores heat generated by the main body 20 and transmits the heat to the outside The ultrasonic probe 10 further includes a battery 40 that supplies power to the main body 20, and a display 50 that displays the amount of heat that is stored in the heat storage 30.

The main body 20 may generate heat due to an electrical circuit or the like during a process of transmitting an ultrasound signal and receiving an echo signal. The amount of heat that is generated by an ultrasonic probe is about 1 W, which is small enough to be naturally released through a case of the ultrasonic probe, whereas when ultrasonic transducers have multiple channels, the amount of heat that is generated when multi-channel transducers are included is as much as about 7 W as described above. Accordingly, about 10 minutes to about 15 minutes after the main body 20 begins to operate, a temperature may increase to about 40° C. to about 45° C. and may injure an operator who holds the main body 20.

The heat storage 30 is a heat dissipation member for absorbing heat that is generated by the main body 20 and dissipating the heat to the outside. Referring to FIG. 2, a first heat transfer part 21 for transferring heat that is generated by the electrical circuit or the like is disposed in the main body 20 to the outside, and is formed on one surface of the main body 20. A second heat transfer part 31 that contacts the first heat transfer part 21 is formed on one surface of the heat storage 30. Each of the first heat transfer part 21 and the second heat transfer part 31 may be formed of a material having excellent thermal conductivity, for example, copper or silver. When the ultrasonic probe 10 is used, heat that is generated by the main body 20 may be absorbed through the first heat transfer part 21 and the second heat transfer part 31 by the heat storage 30, and thus the main body 20 may be maintained at a temperature that is low enough not to injure the operator. The heat storage 30 may be detachably formed and be spaced apart from the main body 20 for heat dissipation. However, the exemplary embodiments are not limited thereto, and the heat storage 30 may be integrally formed with the main body 20.

Referring again to FIG. 1, the battery 40 that is a device for supplying power to the main body 20 may be electrically connected to the main body 20. An ultrasonic probe may be formed in a wired manner and thus may directly receive power. However, as the ultrasonic probe 10 is used in a wireless manner to improve user convenience, the battery 40 for supplying power to the main body 20 is connected to the main body 20. The battery 40 may be detachably or integrally connected to the main body 20. According to an exemplary embodiment, the battery 40 may be fixed to the heat storage 30 and may be attached to or detached from the main body 20 along with the heat storage 30. However, the exemplary embodiments are not limited thereto, and each of the battery 40 and the heat storage 30 may be attached to or detached from the main body 20.

The display 50 is a device for displaying the amount of heat to be transferred from the main body 20 to the heat storage 30. The operator may check the amount of heat that is currently stored in the heat storage 30 and an available time of the ultrasonic probe 10 by using the display 50.

Figure 3:
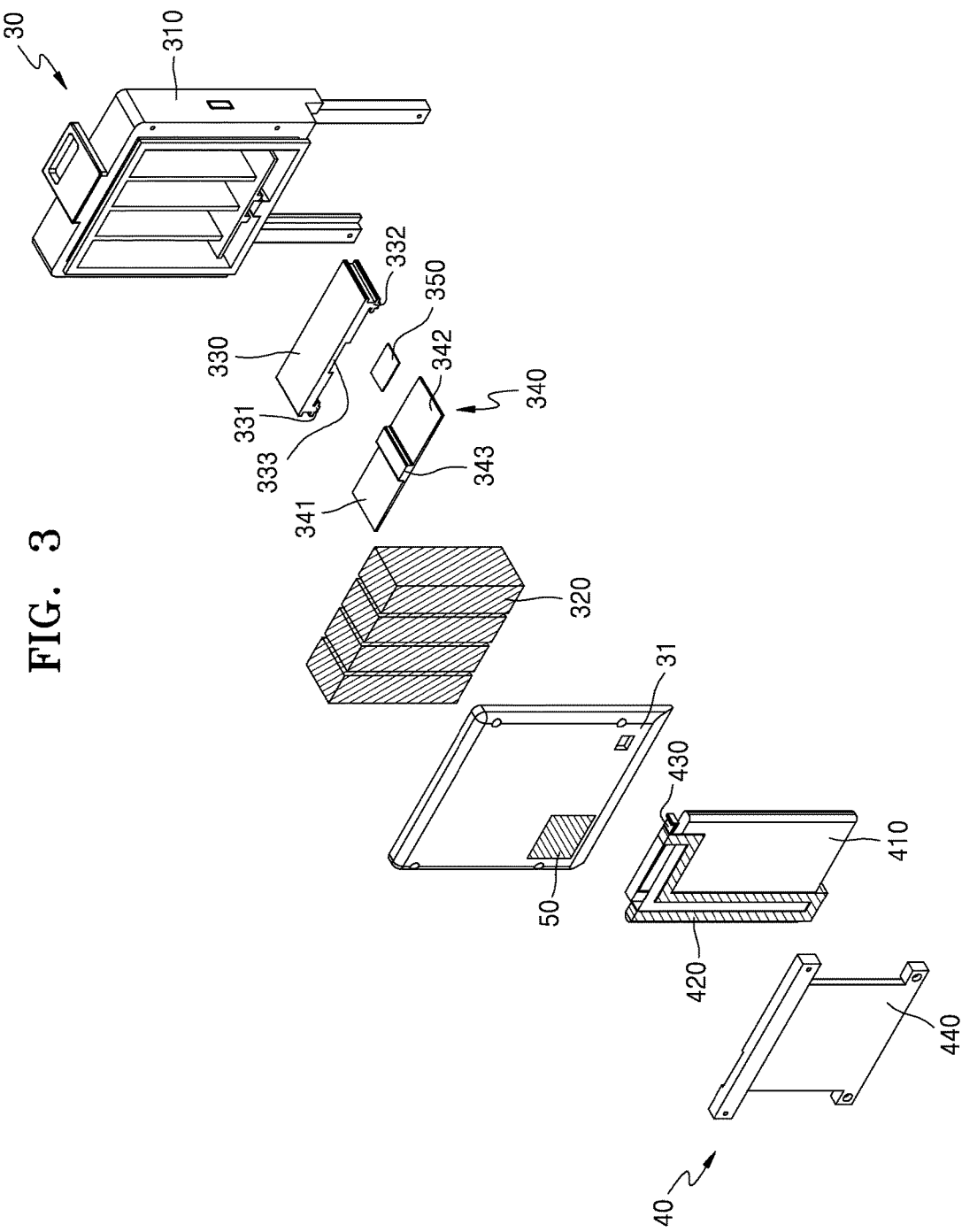
FIG. 3 is an exploded perspective view illustrating a heat storage and a battery, according to an exemplary embodiment.
Figure 4:
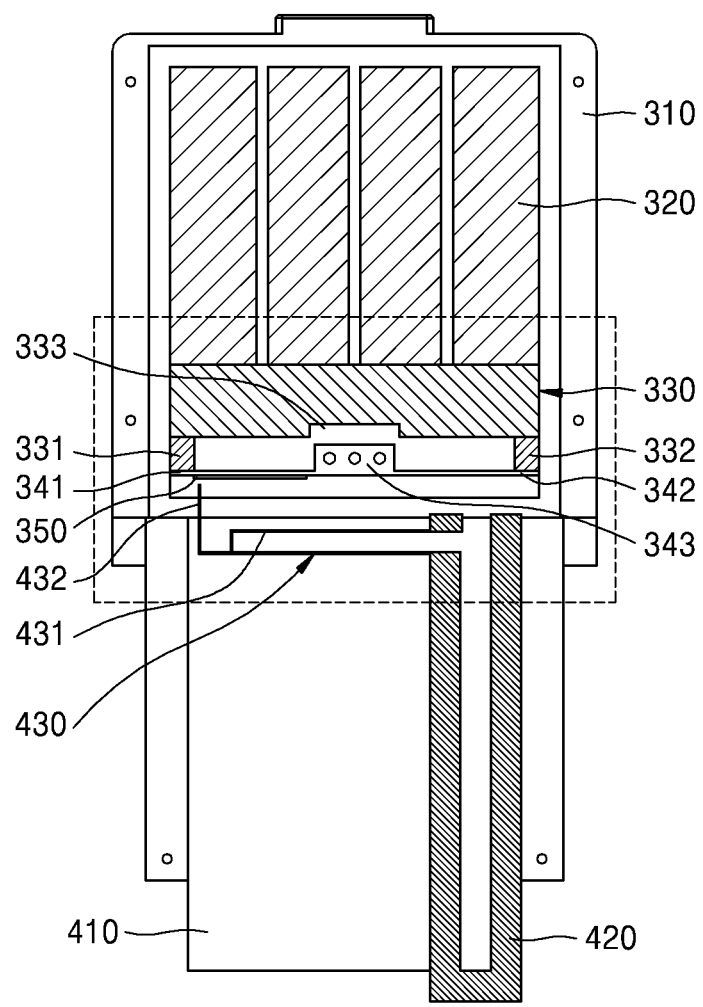
FIG. 4 is a cross-sectional view illustrating the heat storage and the battery of FIG. 3.

FIG. 3 is an exploded perspective view illustrating the heat storage 30 and the battery 40, according to an exemplary embodiment. FIG. 4 is a cross-sectional view illustrating the heat storage 30 and the battery 40 of FIG. 3.

The heat storage 30 includes a heat storage member, for example, a phase-change material 320, which receives heat from the main body 20 and temporarily stores the heat before dissipating the heat to the outside. Referring to FIGS. 3 and 4, the heat storage 30 includes the phase-change material 320 that stores heat received from the main body 20, a housing 310 that accommodates the phase-change material 320, and a piston 330 that is disposed on one end portion of the housing 310, seals the phase-change material 320, and moves in a longitudinal direction of the housing 310. The heat storage 30 further includes an elastic member 340 that is disposed on a lower end portion of the piston 330, and a sensor 350 that detects the amount of deformation of the elastic member 340.

The housing 310 that may accommodate the phase-change material 320 may seal the phase-change material 320 with the second heat transfer part 31 and the piston 330 that are disposed on the housing 310. For example, the housing 310 may have a cylindrical shape. However, the exemplary embodiments are not limited thereto, and the housing 310 may have any shape as long as the piston 330 may move in the housing 310.

The phase-change material 320 refers to a thermoadjustable material such as a latent heat material, a heat storage material, or a cold storage material that may store heat during a phase-change process. The phase-change material 320 may store a lot of thermal energy or release the stored thermal energy during a phase-change process. For example, the phase-change material 320 may store heat or release the stored heat by physically changing from one state to another state, for example, from a solid state to a liquid state, from a liquid state to a solid state, or from a liquid state to a gas state. Examples of the phase-change material 320 may be mainly classified into an organic material and an inorganic material, and may be classified according to an operating temperature into a high-temperature phase-change material (40° C.-150° C.), a medium-temperature phase-change material (0° C.-40° C.), and a low-temperature phase-change material (−60° C.-0° C.). Examples of the organic material may include hydrocarbon-based tetradecane, octadecane, and nonadecane consisting of carbon and hydrogen, and examples of the inorganic material may include calcium chloride that occurs as a hydrate containing six water molecules. According to an exemplary embodiment, an operation is performed while the operator holds the ultrasonic probe 10. In order not to injure the operator during the operation of the ultrasonic probe 10, the ultrasonic probe 10 may undergo phase-change at a temperature that ranges from about 25° C. to about 37° C. Accordingly, a medium-temperature phase-change material such as capric acid, normal-docosane (N-docosane), normal elcosane (N-elcosane), or normal octadecane (N-octadecane) may be used.

The piston 330 may be disposed on a bottom portion of the housing 310, may seal the phase-change material 320 in the housing 310, and may vertically move in the longitudinal direction of the housing 310. A plurality of protrusions 331 and 332 are formed on a surface of the piston 330 that does not contact the phase-change material 320, and a recessed groove 333 is formed in a central portion thereof. When the phase-change material 320 undergoes phase-change and thus a volume of the phase-change material 320 increases, the plurality of protrusions 331 and 332 applies pressure to the elastic member 340, and the recessed groove 333 contacts a fixing part 343 that is provided on the elastic member 340, thereby preventing the piston 330 from moving downward excessively.

The elastic member 340 includes a first elastic member 341 and a second elastic member 342 that contact the plurality of protrusions 331 and 332 of the piston 330 and support the piston 330, and the fixing part 343 that supports the first and second elastic members 341 and 342. For example, the fixing part 343 may extend across the housing 310 so that both end portions of the fixing part 343 are fixed to an inner wall portion of the housing 310.

The first and second elastic members 341 and 342 that are planar members contact the plurality of protrusions 331 and 332, where one end portion of each of the first and second elastic members 341 and 342 is fixed to the fixing part 343 and the other portion of each of the first and second elastic members 341 and 342 supports the piston 330. When the phase-change material 320 undergoes phase-change and a volume of the phase-change material 320 increases, the first and second elastic members 341 and 342 may receive pressure from the plurality of protrusions 331 and 332 and may rotate clockwise or counterclockwise about the one end portions that are fixed to the fixing part 343. When the phase-change material 320 undergoes phase-change and a volume of the phase-change material 320 reduces, the first and second elastic members 341 and 342 rotate in the opposite direction due to a restoring force thereof to return to their original positions.

The fixing part 343 may support the recessed groove 333 of the piston 330, thereby preventing the piston 330 from moving downward excessively. Detailed configurations and operations of the piston 330 and the elastic member 340 will be explained below with reference to FIGS. 5 and 6.

The sensor 350 is a detection member for detecting a distance by which the piston 330 moves and detecting a phase-change process of the phase-change material 320. For example, when a strain gauge or a force sensing resistor (FSR) sensor is used as the sensor 350, the sensor 350 may be disposed on the first or second elastic member 341 or 342 and may detect a phase-change state of the phase-change material 320 by detecting the amount of deformation of the first or second elastic member 341 or 342 or pressure applied to the first or second elastic member 341 or 342. Alternatively, when a pressure sensor is used as the sensor 350, the sensor 350 may detect a phase-change state of the phase-change material 320 by measuring a change in pressure in the housing 310 as the phase-change material 320 undergoes phase-change.

The display 50 may display the amount of heat that is transferred to the phase-change material 320 by using the phase-change state of the phase-change material 320 that is detected by the sensor 350. The display 50 may display a state of the phase-change material 320 by using figures or numbers, or may display a state of the phase-change material 320 by changing a color. The operator may determine an operation method and an operation time by taking into account the amount of heat that is stored in the heat storage 30, that is, the phase-change material 320, and displayed on the display 50. A method performed by the display 50 to display a state of the phase-change material 320, and a detailed configuration and operation for determining an operation method and an operation time will be explained below with reference to FIGS. 7 and 9.

Referring to FIGS. 3 and 4, the battery 40 that is a member for supplying power to the main body 20 includes a battery main body 410, and a terminal part 420 that contacts a terminal part formed on the main body 20 and supplies power. The battery 40 further includes a switch 430 that may break electrical connection of the terminal part 420, and a battery cover 440 that covers the battery main body 410.

The switch 430 includes a first connection part 431 and a second connection part 432 that are conductive and are connected to end portions of the terminal part 420. The second connection part 432 may contact the first elastic member 341 that is deformed as the piston 330 moves downward due to phase-change of the phase-change material 320. In this case, the second connection part 432 may be separated from the first connection part 431, and thus power supply to the main body 20 may be cut off. A detailed configuration and operation of the switch 430 for cutting off power supply to the main body 20 will be explained below with reference to FIGS. 5 and 6.

Figure 5:
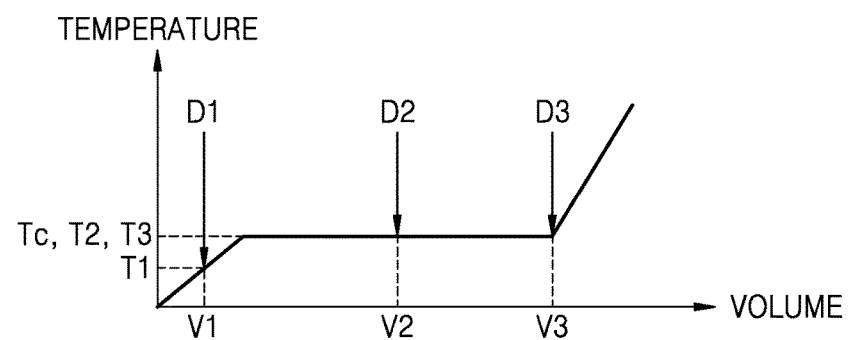
FIG. 5 is a graph illustrating a correlation between a temperature and a volume of a phase-change material, according to an exemplary embodiment.
Figure 6A:
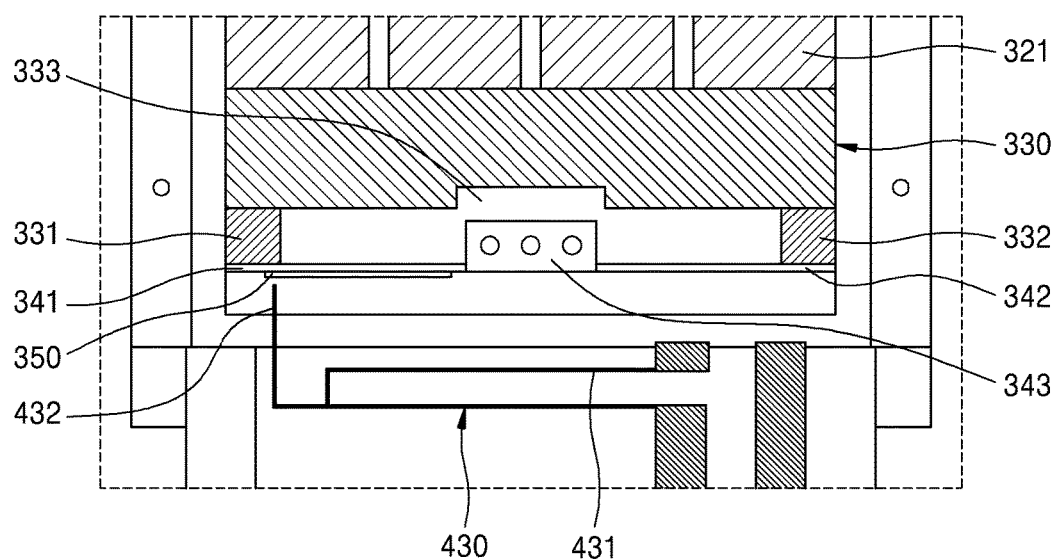
FIGS. 6A through 6C are partial cross-sectional views illustrating the heat storage and the battery of FIG. 3 in first through third states of the phase-change material of FIG. 5.
Figure 6B:
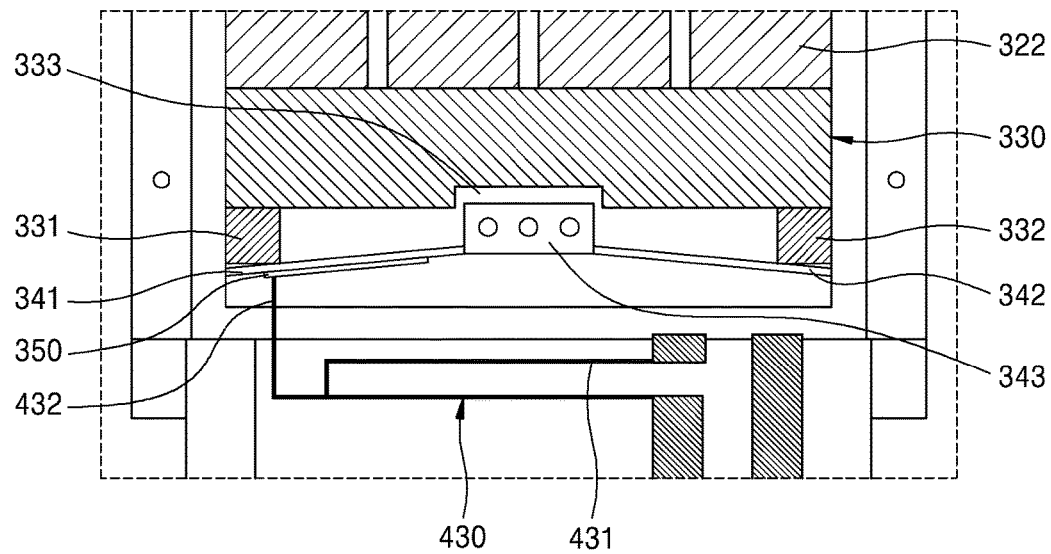
Figure 6C:
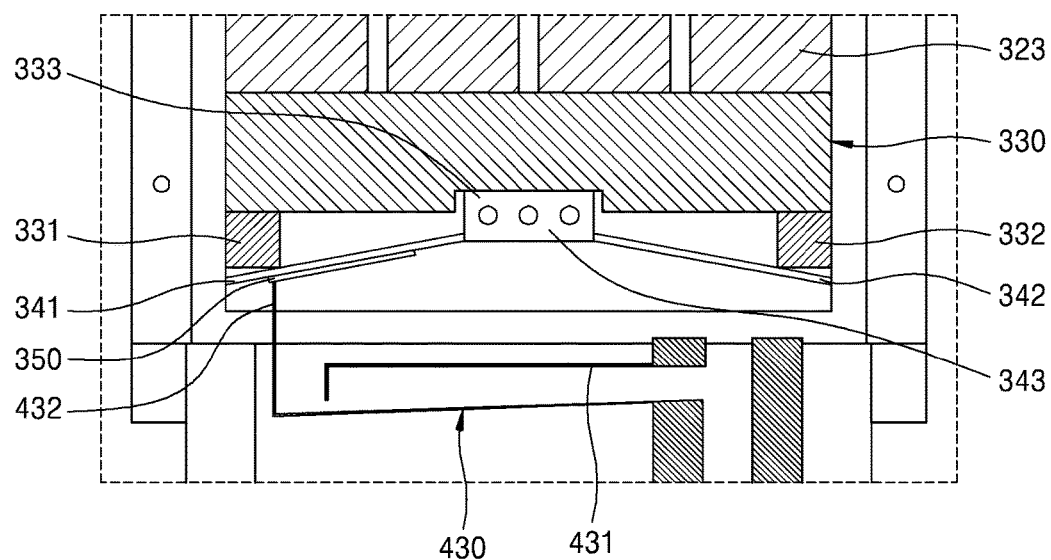

FIG. 5 is a graph illustrating a correlation between a temperature (T) and a volume (V) of the phase-change material 320, according to an exemplary embodiment. FIGS. 6A through 6C are partial cross-sectional views illustrating the heat storage 30 and the battery 40 of FIG. 3 in first through third states D1 through D3 of the phase-change material 320 of FIG. 5.

As the operator uses the ultrasonic probe 10, the amount of heat that is transferred to the phase-change material 320 through the first heat transfer part 21 and the second heat transfer part 31 may increase, and thus the phase-change material 320 may undergo phase-change. Referring to FIGS. 5 and 6A, in the first state D1 that is a state before the operator uses the ultrasonic probe 10, a first temperature T1 of a first phase-change material 321 is the same as an ambient temperature, for example, 25° C. In this case, the first phase-change material 321 is maintained in a solid state. Accordingly, a first volume V1 of the first phase-change material 321 may be maintained at a smallest volume.

Referring to FIG. 6A, as the first volume V1 of the first phase-change material 321 is maintained at the smallest volume in the first state D1, the piston 330 does not move downward. Accordingly, the first and second elastic members 341 and 342 that contact the plurality of protrusions 331 and 332 of the piston 330 is not deformed, and the second connection part 432 of the switch 430 that is disposed adjacent to the first elastic member 341 is still spaced apart from the first elastic member 341. Because the second connection part 432 and the first elastic member 341 are spaced apart from each other, the first connection part 431 and the second connection part 432 are continuously connected to each other, and thus power supply from the battery 40 to the main body 20 may be continued.

Referring to FIGS. 5 and 6B, in the second state D2 that is a state after the operator uses the ultrasonic probe 10, a second temperature T2 of a second phase-change material 322 is the same as a phase-change temperature Tc. The phase-change temperature Tc may vary depending on a type of the phase-change material 320, and a material having any of the various phase-change temperatures Tc may be selected as the phase-change material 320 according to a purpose and an environment for which and in which the ultrasonic probe 10 is used. For example, when the ultrasonic probe 10 is held by the operator while being used, a material having the phase-change temperature Tc that is equal to or lower than 37° C. may be selected to prevent the operator from being injured by a high temperature. In this case, the second phase-change material 322 may be maintained in a state between a solid state and a liquid state, and a second volume V2 of the second phase-change material 322 is greater than the first volume V1 in the first state D1.

Referring to FIG. 6B, as the second volume V2 of the second phase-change material 322 in the second state D2 is greater than the first volume V1 of the first phase-change material 321 in the first state D1, the piston 330 moves downward. In this case, the first and second elastic members 341 and 342 that contact the plurality of protrusions 331 and 332 of the piston 330 are also deformed downward. However, because the second connection part 432 of the switch 430 that is disposed adjacent to the first elastic member 341 is still spaced apart from the first elastic member 341, the first connection part 431 and the second connection part 432 are continuously connected to each other and thus power supply from the battery 40 to the main body 20 may be continued.

Referring to FIGS. 5 and 6C, in the third state D3 that is a state after the operator uses the ultrasonic probe 10, a third temperature T3 of a third phase-change material 323 is still the same as the phase-change temperature Tc. Although heat is continuously applied from the main body 20 to the phase-change material 320 and the phase-change material 320 undergoes phase-change, that is, changes from a solid state to a liquid state, the third temperature T3 may still be the same as the second temperature T2 that is the same as the phase-change temperature Tc. In this case, the third phase-change material 323 is in a liquid state, and a third volume V3 of the third phase-change material 323 increases to be greater than the second volume V2 in the second state D2. However, because the third phase-change material 323 in the third state D3 is completely in a liquid state, if heat is additionally applied form the main body 20, a temperature of the phase-change material 320 may increase to be higher than the phase-change temperature Tc, thereby injuring the operator.

Referring to FIG. 6C, as the third volume V3 of the third phase-change material 323 in the third state D3 increases to be greater than the second volume V2 of the second phase-change material 322 in the second state D2, the piston 330 moves downward. In this case, the first and second elastic members 341 and 342 that contact the plurality of protrusions 331 and 332 of the piston 330 are also additionally deformed. However, because the recessed groove 333 of the piston 330 contacts and is supported by the fixing part 343 of the elastic member 340, even when heat is additionally applied from the main body 20 to the phase-change material 320, the piston 330 does not move downward. Also, the second connection part 432 of the switch 430 that is disposed adjacent to the first elastic member 341 contacts the first elastic member 341, and moves downward. As a result, the first connection part 431 and the second connection part 432 are separated from each other and power supply from the battery 40 to the main body 20 is cut off. Accordingly, even when the operator continuously performs an operation without recognizing a state of the ultrasonic probe 10, power supply is automatically cut off, and thus the ultrasonic probe 10 may stop working. Accordingly, heat may not be additionally applied from the main body 20 to the phase-change material 320, and a temperature of the phase-change material 320 may be prevented from being increased, thereby preventing the operator from being injured.

Figure 7A:
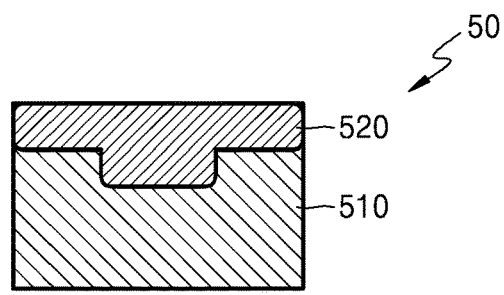
FIGS. 7A through 7C are front views illustrating a display in the first through third states of the phase-change material of FIG. 5, according to an exemplary embodiment.
Figure 7B:
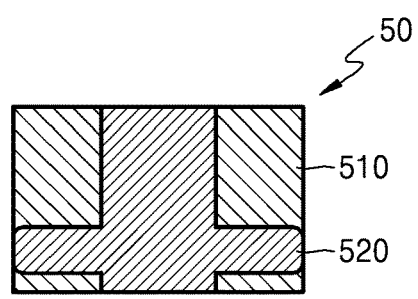
Figure 7C:
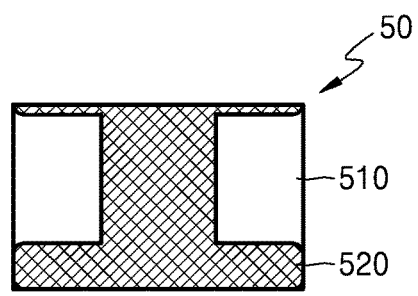
Figure 8:
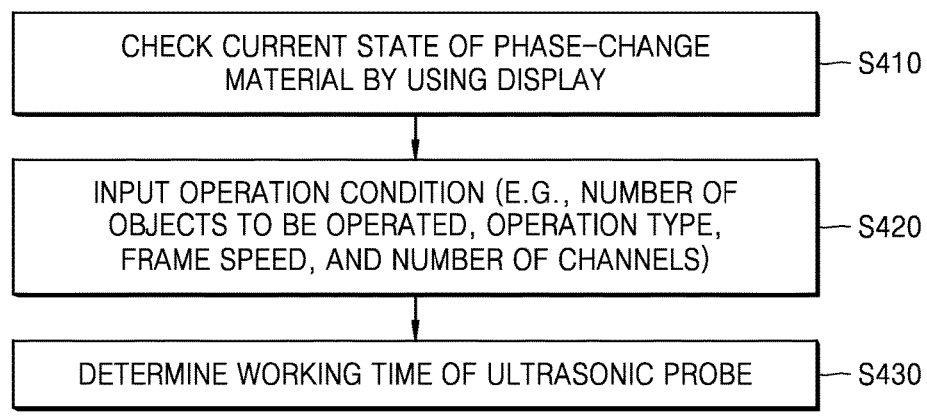
FIG. 8 is a flowchart for determining a method of using the ultrasonic probe of FIG. 1, according to an exemplary embodiment.

FIGS. 7A through 7C are partial front views illustrating the display 50 in the first through third states D1 through D3 of FIG. 5, according to an exemplary embodiment. FIG. 8 is a flowchart for determining a method of using the ultrasonic probe 10 of FIG. 1, according to an exemplary embodiment.

As described above, as the operator uses the ultrasonic probe 10, the phase-change material 320 changes among the first through third states D1 through D3. In this case, when the operator may recognize a state of the phase-change material 320 that is detected from the sensor 350, the operator may alter an operation time and an operation condition of the ultrasonic probe 10, thereby enabling the operator to use the ultrasonic probe 10 in an optimum environment. Referring to FIGS. 7A through 7C, because the display 50 is disposed on a front surface of the heat storage 30, the operator may recognize a state of the phase-change material 320. For example, the display 50 includes a first display 510 and a second display 520 that show shapes of the housing 310 and the piston 330, respectively. Before the operator uses the ultrasonic probe 10, because the second display 520 is disposed over the first display 510, the operator may recognize that the phase-change material 320 is in the first state D1. When the operator uses the ultrasonic probe 10 and heat is applied to the phase-change material 320, the second display 520 moves downward, and thus the operator may recognize that the phase-change material 320 changes from the first state D1 to the second state D2. When the operator uses the ultrasonic probe 10 and heat is continuously applied to the phase-change material 320, the second display 520 moves to a lower end portion, and thus the operator may recognize that the phase-change material 320 changes from the second state D2 to the third state D3. In this case, the first connection part 431 and the second connection part 432 may be separated from each other, and power supply from the battery 40 to the main body 20 may be cut off, thereby preventing the operator from being injured.

Referring to FIGS. 7A through 7C and FIG. 8, the amount of heat that is applied from the main body 20 to the phase-change material 320 may be determined according to a time and an environment for which and in which the main body 20 operates. Accordingly, the operator may check a state of the phase-change material 320 on the display 50 and may determine an operation method and an operation time.

According to an exemplary embodiment, in operation S410, a current state of the phase-change material 320 is checked by using the display 50. For example, the operator may check a state of the phase-change material 320 on the display 50 and may check a residual heat capacity of the phase-change material 320.

In operation S420, an operation condition is input by taking into account an environment in which the ultrasonic probe 10 is used. For example, the operator may input the number of objects to be operated by the ultrasonic probe 10 and an operation type of the ultrasonic probe 10. In addition, the quality of an image to be obtained may vary according to an operation type and a state of an object to be operated. Also, when a frame speed or the number of channels of the ultrasonic probe 10 increases, an image having a higher resolution may be obtained. Accordingly, a frame speed or the number of channels by which an image may be obtained may be input.

In operation S430, an operation or working time of the ultrasonic probe 10 is determined by taking into account the residual heat capacity of the phase-change material 320 and the input operation condition.

The amount of heat that may be generated according to the number of objects to be operated, an operation type, a frame speed, and the number of channels may be stored in a memory. Accordingly, once an operation condition is input, a total amount of generated heat that matches the operation condition may be calculated, and a working time of the ultrasonic probe 10 may be determined by taking into account a residual heat capacity of the phase-change material 320 that is displayed on the display 50. Accordingly, the operator may complete an operation within the determined working time, and the operator may increase or reduce the working time of the ultrasonic probe 10 by altering the operation condition.

Figure 9A:
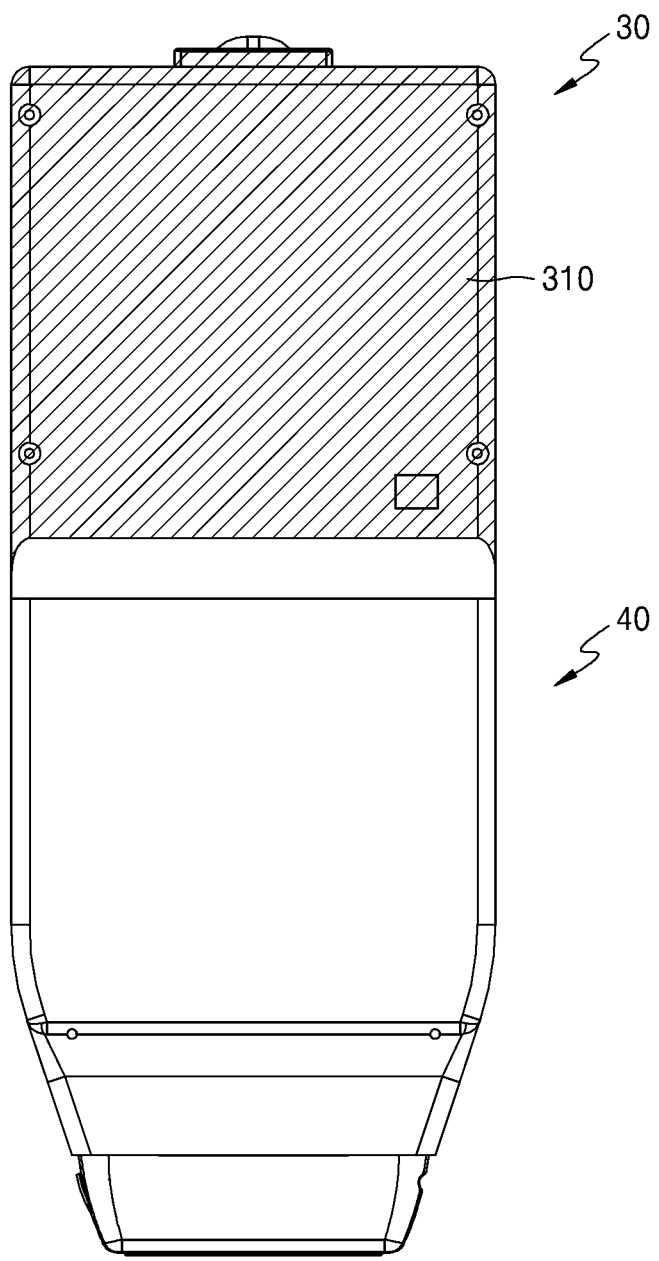
FIGS. 9A through 9C are front views illustrating the ultrasonic probe of FIG. 1 in the first through third states of the phase-change material of FIG. 5, according to an exemplary embodiment.
Figure 9B:
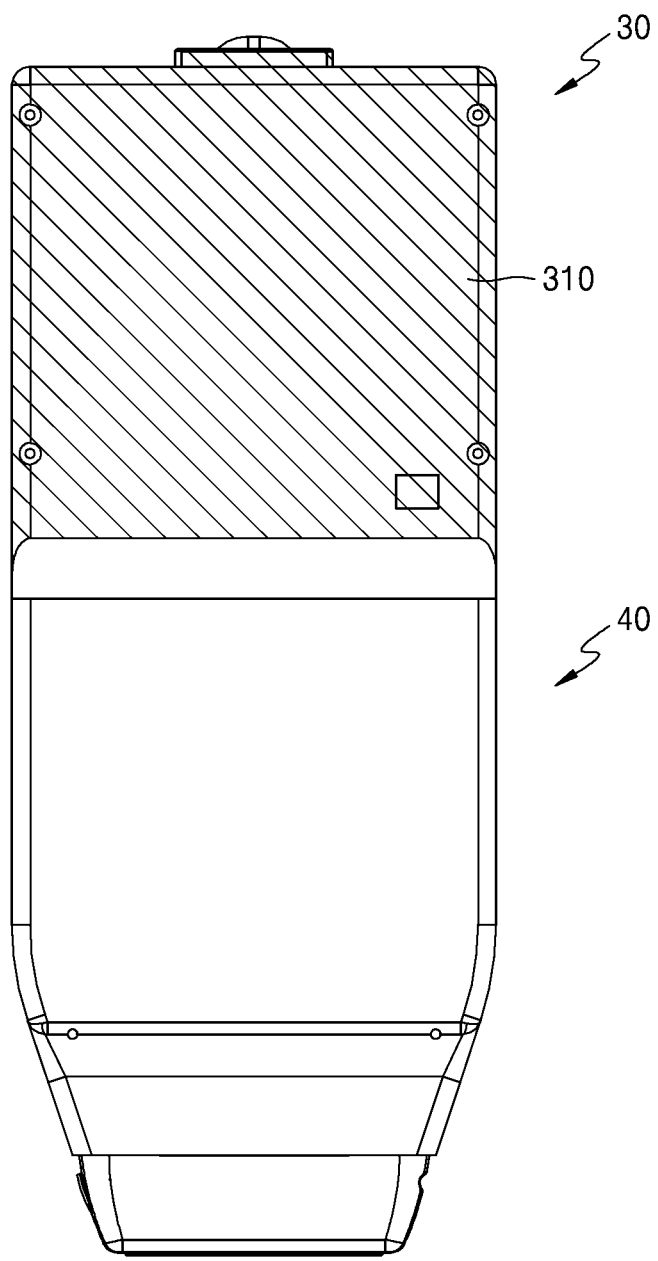
Figure 9C:
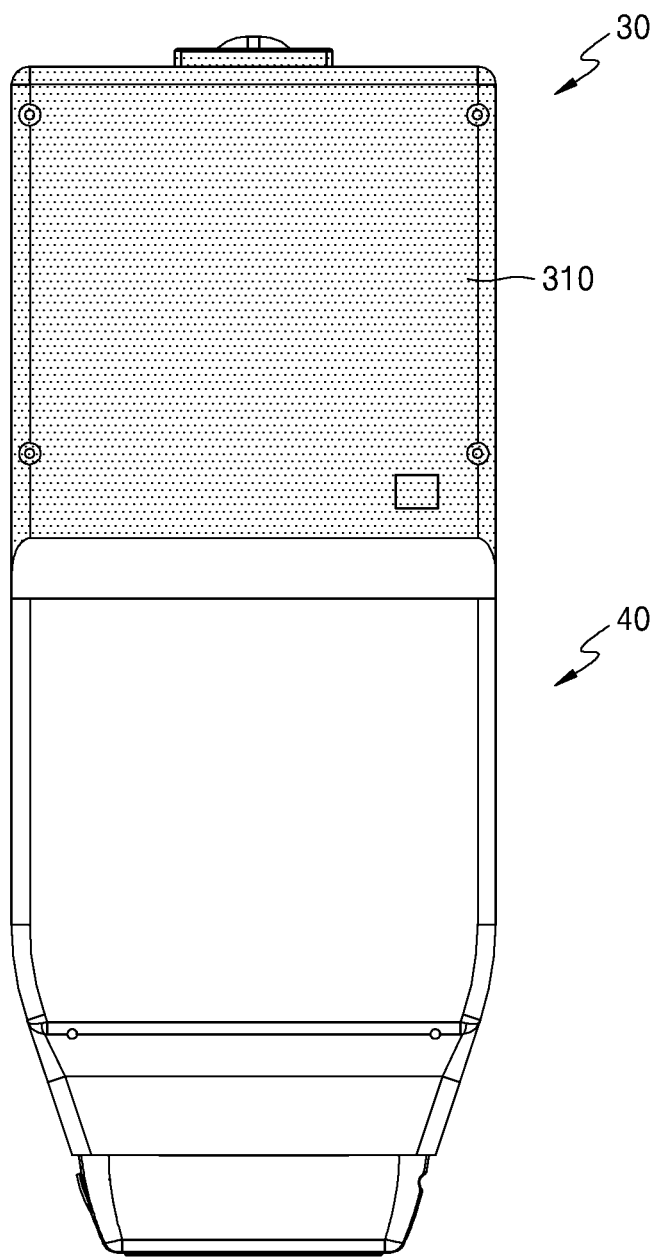

FIGS. 9A through 9C are front views illustrating the ultrasonic probe 10 of FIG. 1 in the first through third states D1 through D3 of FIG. 5, according to an exemplary embodiment.

As described above, the display 50 may display a state of the phase-change material 320 by using figures or numbers or by changing a color. Referring to FIGS. 9A through 9C, for example, it is displayed that a state of the phase-change material 320 is changed by changing a color of the housing 310 of the heat storage 30. The housing 310 may be formed of reflex electronics skin or PDF ink whose color may be changed when receiving a control signal. The housing 310 receives a state of the phase-change material 320 that is detected from the sensor 350, and changes its color, and the operator may more easily check the state of the phase-change material 320 by observing the change in the color of the housing 310. However, an area whose color may be changed is not limited to the housing 310, and any area whose outer appearance may be observed by the operator may be used.

A process of changing the housing 310 according to a state of the phase-change material 320 and a process of determining a method of using the ultrasonic probe 10 by using the state of the phase-change material 320 that is checked by observing a color of the housing 310 are the same as those described with reference to FIGS. 7 and 8, and thus an explanation thereof will not be given.

Figure 10A:
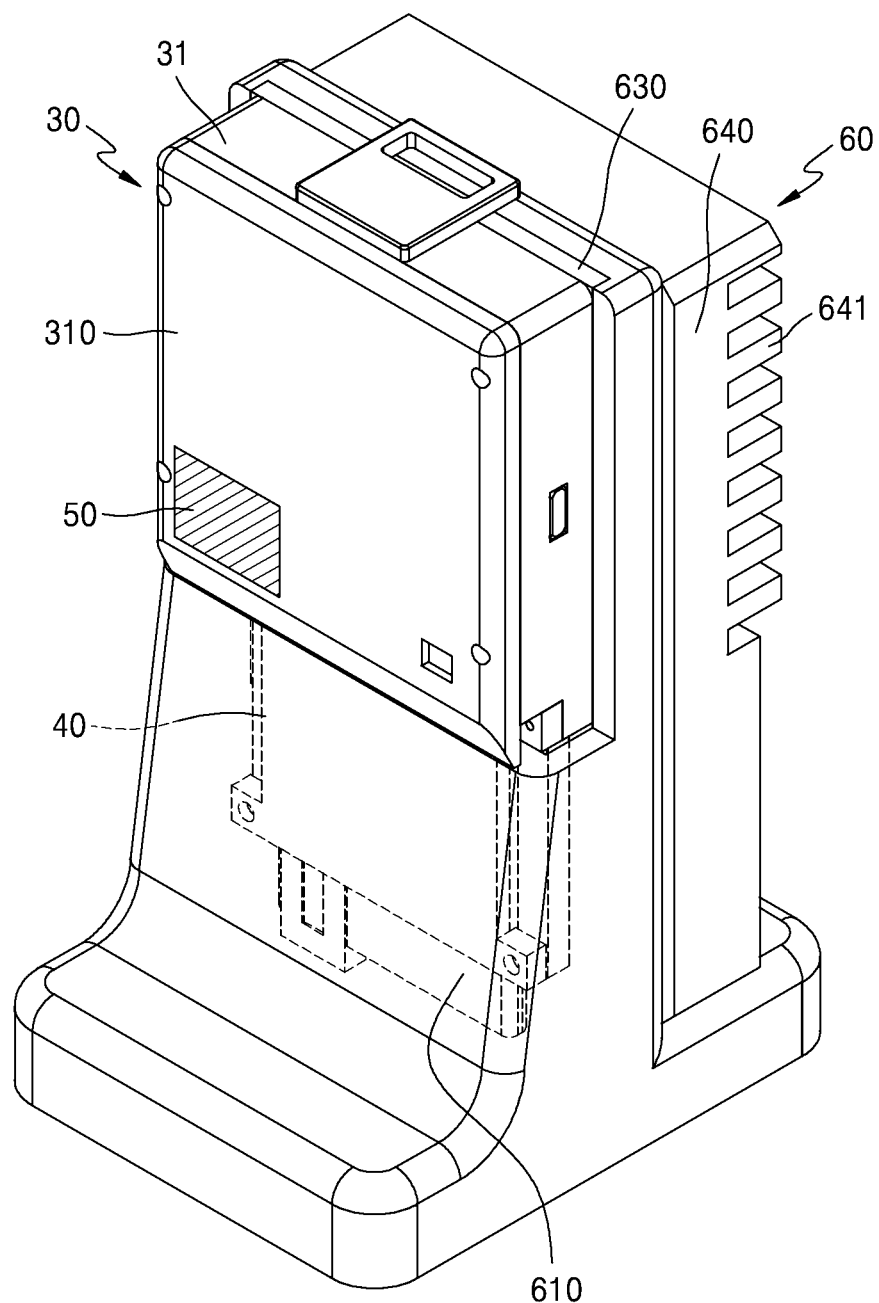
FIG. 10A is an assembled perspective view illustrating the heat storage and the battery of FIG. 3 that are mounted on a mounting device, according to an exemplary embodiment.
Figure 10B:
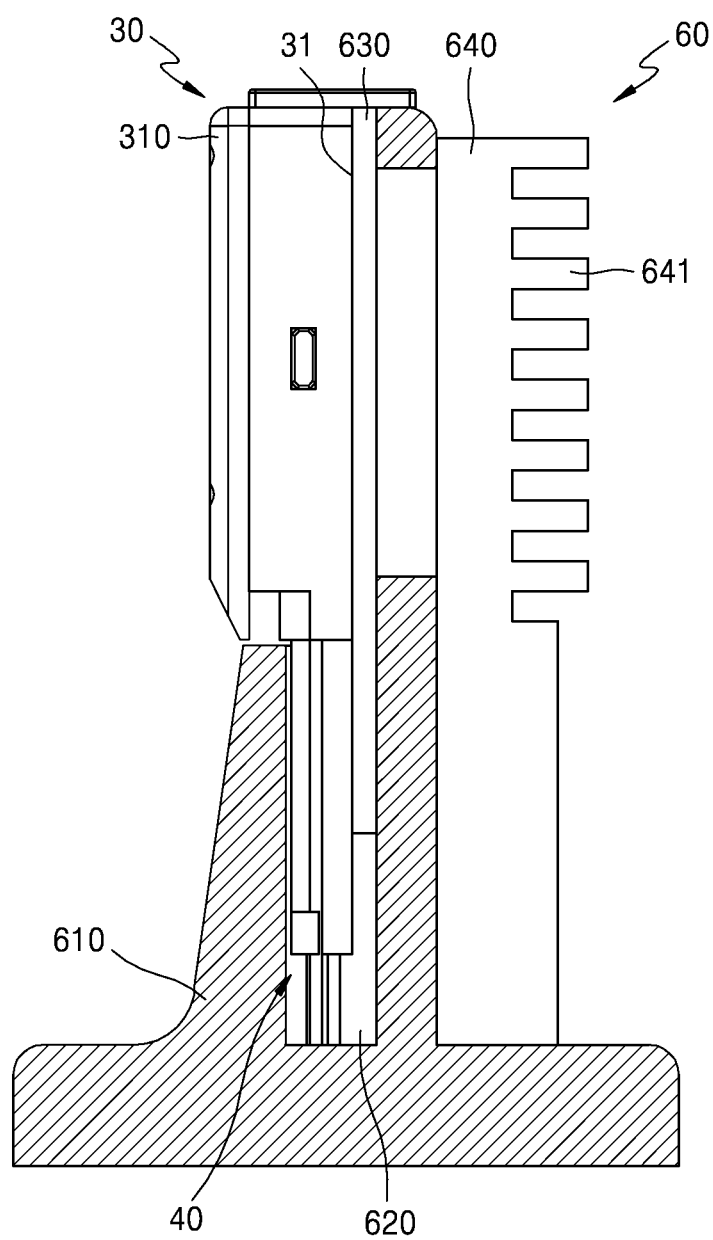
FIG. 10B is a cross-sectional view illustrating the mounting device, the heating storage, and the battery of FIG. 10A.

FIG. 10A is an assembled perspective view illustrating the heat storage 30 and the battery 40 of FIG. 3 that are mounted on a mounting device 60, according to an exemplary embodiment. FIG. 10B is a cross-sectional view illustrating the mounting device 60 of FIG. 10A.

To release heat from the heat storage 30 to the outside or to charge the battery 40, the heat storage 30 or the battery 40 may be coupled to a separate apparatus. Referring to FIGS. 10A and 10B, the mounting device 60 includes an insertion part 610 into which and by which the battery 40 is inserted and supported, and a charger 620. The charger 620 may use a wired method in which the charger 620 may directly contact the terminal part 420 of the battery 40 and may charge the battery 40, or a wireless method in which a transmission coil and a reception coil having the same resonance frequency may be respectively disposed on the battery 40 and the charger 620 and the charger 620 may charge the battery 40. Also, the mounting device 60 includes a third heat transfer part 630 that contacts the second heat transfer part 31 of the heat storage 30 and receives heat from the phase-change material 320, and a heat dissipator 640 that receives heat from the third heat transfer part 630 and dissipates the heat to the outside.

The insertion part 610 is a member for supporting the heat storage 30 and the battery 40. For example, only the battery 40 is inserted into the insertion part 610, the exemplary embodiments are not limited thereto. If both the heat storage 30 and the battery 40 may be inserted into the insertion part 610, or the main body 20, the heat storage 30, and the battery 40 are integrally provided, the ultrasonic probe 10 may be inserted into the insertion part 610.

The third heat transfer part 630 that may contact the second heat transfer part 31 and may transfer heat that is stored in the phase-change material 320 to heat dissipation fins 640 may be formed of copper or silver having high thermal conductivity.

The heat dissipator 640 is a heat dissipation member for dissipating heat received from the third heat transfer part 630 to the outside. For example, the heat dissipator 640 includes a plurality of heat dissipation fins 641 to increase a contact area with external air, and thus may more efficiently release heat transferred from the third heat transfer part 630 to the outside.

As the heat storage 30 and the battery 40 are coupled to each other on the mounting device 60, heat that is stored in the heat storage 30 may be dissipated through the heat dissipator 640 to the outside and a temperature of the phase-change material 320 may be reduced. Also, when the battery 40 is coupled to the charger 620 of the mounting device 60, because heat dissipation and charging of the battery 40 may be simultaneously performed, the operator may efficiently use a time. In addition, because a state of the phase-change material 320 may be checked by observing a change in a color of the display 50 or the housing 310, heat dissipation of the phase-change material 320 may be more easily checked, and the heat storage 30 may be separated from the mounting device 60 during an operation.

The foregoing exemplary embodiments and advantages are exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasonic probe comprising:
    a main body configured to transmit and receive ultrasound;
    a heat storage comprising a phase-change material configured to store heat being generated by the main body;
    a display configured to display an amount of the stored heat; and
    a battery configured to supply power to the main body,
    wherein the battery comprises a switch configured to control an electrical connection with the main body, and turn on and turn off according to a change in a volume of the phase-change material,
    wherein the switch is configured to turn off the power to the main body in response to a phase change of the phase-change material being complete,
    wherein the heat storage comprises a piston configured to move according to a change in a volume of the phase-change material, and
    wherein the switch turns on and off according to the movement of the piston.

2. The ultrasonic probe of claim 1, wherein the battery is configured to be attached to the heat storage, and
    the battery and the heat storage are configured to be attached to and detached from the main body.

3. The ultrasonic probe of claim 1, wherein the switch comprises:
    a first connection part, and
    a second connection part configured to:
    contact the first connection part to turn on the switch; and
    separate from the first connection part to turn off the switch, according to the movement of the piston.

4. The ultrasonic probe of claim 3, wherein the heat storage further comprises an elastic member configured to move and contact the second connection part, according to the movement of the piston, and
    the second connection part is configured to separate from the first connection part to turn off the switch, according to the movement and the contact of the elastic member.

5. The ultrasonic probe of claim 1, further comprising a sensor configured to:
    detect the movement of the piston; and
    detect the change in the volume of the phase-change material.

6. The ultrasonic probe of claim 1, wherein the display is configured to change in color, according to the detected change in the volume of the phase-change material.

7. The ultrasonic probe of claim 1, wherein the heat storage further comprises a housing configured to change in color, according to the detected change in the volume of the phase-change material.

8. The ultrasonic probe of claim 1, wherein the display is configured to display the movement of the piston.

9. The ultrasonic probe of claim 1, wherein a temperature of a phase-change is greater than or equal to 25° C. and is less than or equal to 37° C.

10. A mounting device on which the ultrasonic probe of claim 1 is mounted, the mounting device comprising:
 an insertion part into which the heat storage is inserted; and
 a heat dissipator configured to dissipate the stored heat.

11. The mounting device of claim 10, wherein the ultrasonic probe further comprises a battery configured to supply power to the main body, and
 the mounting device further comprises a charger configured to charge the battery.

12. The mounting device of claim 11, wherein the charger is configured to charge the battery, using a wireless or wired method.

13. The mounting device of claim 11, wherein the dissipation of the stored heat by the heat dissipator and the charge of the battery by the charger are simultaneously performed.

14. The mounting device of claim 10, wherein the display is configured to display an amount of the dissipated heat.

15. An ultrasonic probe comprising:
 a main body configured to transmit and receive ultrasound;
 a phase-change material configured to store heat being generated by the main body;
 a display configured to display a state of the phase-change material; and
 a battery configured to supply power to the main body,
 wherein the battery comprises a switch configured to control an electrical connection with the main body, and turn on and turn off according to a change in a volume of the phase-change material; and
 a piston configured to move according to a change in a volume of the phase-change material,
 wherein the switch is configured to turn off to cut off the power to the main body in response to a phase change of the phase-change material being complete, and
 wherein the switch turns on and off according to the movement of the piston.

* * * * *